United States Patent [19]
Rajan et al.

[11] Patent Number: 5,543,324
[45] Date of Patent: Aug. 6, 1996

[54] MICROBIALLY MEDIATED DEGRADATION OF NITROGEN-CONTAINING PHENOL COMPOUNDS

[75] Inventors: Janardhanan S. Rajan; Fateme S. Sariaslani, both of Newark, Del.

[73] Assignee: E. I. Du Pont de Nemours and Company, Wilmington, Del.

[21] Appl. No.: 396,442

[22] Filed: Feb. 28, 1995

Related U.S. Application Data

[63] Continuation of Ser. No. 6,092, Jan. 15, 1993, abandoned.
[51] Int. Cl.$^6$ .................. C12N 1/20; C12N 1/12
[52] U.S. Cl. .................. 435/252.4; 435/253.3; 435/262.5; 435/830; 435/874
[58] Field of Search .................. 435/262.5, 252.4, 435/253.3, 830, 874

[56] References Cited

U.S. PATENT DOCUMENTS

| | | | |
|---|---|---|---|
| 4,535,061 | 8/1985 | Chakrabarty et al. | 435/253 |
| 5,085,998 | 2/1992 | Lebron et al. | 435/262 |

OTHER PUBLICATIONS

H. H. Tabak et al., *J. of Bacteriology*, 87(1):910 (1964).
B. B. Westfall, *J. Pharmacol. Exp. Therap.*, 78:386 (1943).
P. C. Kearny et al., *Chemosphere*, 12(11/12):1583 (1983).
D. Erikson, *J. Bact.*, 41:277 (1941).
F. W. Moore, *J. Gen. Microbiol.*, 3:143 (1949).
W. W. Westerfeld et al., *J. Biol. Chem.*, 227:379 (1957).
J. F. Wyman et al., *Applied and Environmental Microbiology*, 37(2):222 (1979).
H. Lenke et al., *Applied and Environmental Microbiology*, 58(9):2928 (1992).
K. Gundersen et al., *Acta. Agric. Scand.*, 6:100 (1956).
H. Lenke et al., *Applied and Environmental Microbiology*, 58(9):2933 (1992).
Hanne, L. F. et al, *Applied and Environmental Microbiology*, 59(10), 3505–3508, Oct. 1993.
Tabak, H. H. et al, *J. of Bacteriology*, 87(1), 910 (1964).
Westfall, B. B., *J. Pharmacol. Exp. Therap.*, 78, 386 (1943).
Kearney, P. C. et al, *Chemosphere*, 12(11/12), 1583 (1983).
Moore, F. W., *J. Gen. Microbiol.*, 3, 143 (1949).
Westerfeld, W. W. et al, *J. Biol. Chem.*, 227, 379 (1957).
Hanne, et al, *Applied and Environmental Microbiology*, 59(10), 3505–3508 (1993).
Zeyer, J. et al, *J. Agric. Food Chem.*, 32, 238–242 (1984).
Heitkamp, M. A. et al, *Applied and Environmental Microbiology*, 56(10), 2967–2973 (1990).
Raymond, D. G. M. et al, *Pesticide Biochemistry and Physiology*, Academic Press, NY, 1(2), 123–130 (1971).
Goodfellow, M. and Mordarski, M., Eds., *The Biology of the Actinomycetes*, Academic Press, NY; 77–79 and 91–94 (1984).
Heitkamp et al, Applied and Environmental Microbiology, 56(10):2967–73 (1990, Oct.).
Zeyer et al, J. of Agricultural and Food Chem., 32(2):238–42 (1984).
Raymond et al, Pesticide Biochem. and Physiol., 1:123–130 (1971, Sep.).
Goodfellow et al (Ed.), The Biology of the Actinomycetes, Academic Press: New York, 1984, pp. 77–79 and 91–94.

*Primary Examiner*—Michael G. Wityshyn
*Assistant Examiner*—L. Blaine Lankford

[57] ABSTRACT

Nitrogen-containing phenol compounds are biodegradable by a consortium of microorganisms. The consortium was isolated from waste sludge by successive subculturing into medium containing picric acid as the only carbon source. During the period of degradation, picric acid was seen to degrade to a colored intermediate which later disappeared. UV-Vis spectrometry, HPLC and GC-mass spectrophotometry showed that the entire ring structure was eventually destroyed. The consortium contains microorganisms from the genera Arthrobacter, Avrobacterium and Pseudomonas.

2 Claims, 3 Drawing Sheets

MICROBIALLY MEDIATED DEGRADATION OF NITROGEN-CONTAINING PHENOL COMPOUNDS

This a continuation of application Ser. No. 08/006,092 filed Jan. 15, 1993, now abandoned.

FIELD OF INVENTION

The present invention relates to the microbial-mediated degradation of picric acid and other nitrogen substituted phenols by a consortium of microbes. More specifically, a defined mixture of bacteria have been isolated that have the ability to use picric acid as a sole carbon source and completely degrade picric acid to the level where no aromatic degradation products can be detected.

BACKGROUND

Picric acid (2,4,6-trinitrophenol) is a compound used in a variety of industrial applications including the manufacture of explosives, aniline, color fast dyes, pharmaceuticals and in steel etching. Picric acid and ammonium picrate were first obtained as fast dyes for silk and wool. However, the unstable nature of picric acid was soon exploited for use as an explosive and explosive boosters where it is the primary component of blasting caps which are used for the detonation of 2,4,6-Trinitrotoluene (TNT). Because of its explosive nature, disposal of waste picric acid poses unique hazards not generally associated with other environmental toxicants.

Mounting public concern and increasing government regulations have provided the impetus for a safe, effective means to remediate picric acid contaminated environments. Past methods of disposing of munitions and other wastes containing picric acid have included dumping at specified land-fill areas, isolation in suitable, reinforced containers, land based deep-welling, dumping in deep water at sea and incineration. All of these methods carry some potential for harm to the environment. For example, incineration creates a problem of air pollution and disposal on land risks the possibility that toxic substances will elute or leach into locations where they may threaten aquatic life forms, animals or humans. A more desirable disposal method might incorporate a chemical or enzymatic degradative process.

The metabolic reduction of organic nitrogen groups has been known for some time. Westfall, *J. Pharmacol. Exp. Therap.*, 78:386 (1943) reported that liver, kidney and heart tissue are active in the reduction of trinitrotoluene, however, was not able to identify the specific enzyme system responsible. Westerfield et al., *J. Biol. Chem.*, 227:379 (1957) further disclosed that purified xanthine oxidase is capable of reducing organic nitrogen groups and demonstrated that the molybdenum (Mo) co-factor was essential in the degradative process.

Microbial degradation of organic nitrogen compounds has been limited to a handful of organisms. Erickson, *J. Bact.*, 41:277 (1941) reported that certain strains of Micromonospora were able to utilize picric acid and trinitro-resorcinol as a carbon source and Moore. *J. Gen. Microbiol.*, 3:143 (1949) described two unspecified proactinomnycetes as being capable of using nitrobenzene as a simultaneous source of carbon and nitrogen. Gundersden et al., *Acta. Agric. Scand.*, 6:100 (1956) described the metabolism of picric acid by Corynebacterium simplex which was isolated from soil as a 4,6-dinitro-2-methylphenol-degrading organism. Degradation was determined by measuring the amount of nitrate produced when the organism was contacted with an organic nitrogen compound. The extent of degradation and the identification of specific degradation products were not reported. Later, Wyman et al., *Appl. Environ. Microbiol.*, 37(2):222 (1979) found that a strain of pseudomonas aeruginosa reduced picric acid to 2-amino-4,6-dinitrophenol (picramic acid) under anaerobic conditions. Wyman further determined that degradation products from both picric and picramic acid produced by this strain demonstrated mutagenicity as assayed by the standard AMES test. Another pseudomonas sp., *P. putida*, has been shown to be able to use picric acid as a carbon source and achieve some bioconversion of the compound to 1,3,5-trinitro benzene, 2,4,6-trinitroaldehyde, and 3,5-dinitrophenol. Kearney et al., *Chemosphere*, 12 (11–12):1583 (1983).

Most recently, *Rhodococcus erythropolis* has been identified as a picric acid degrading bacteria. Lenke et al., *Appl. Environ. Microbiol.*, 58(9):2933 (1992) teach that *R. erythropolis*, under aerobic conditions, can incompletely utilize picric acid as a nitrogen source producing nitrite and 2,4,6-trinitro-cyclohexanone, which cannot be degraded further.

In spite of the investigative activity in the area of microbial degradation of picric acid and other organic nitrogen compounds, there remain several difficulties to overcome before any of the above mentioned microbial systems can be used for the effective remediation of contaminated environments. All of the microbes investigated are isolated organisms and, although they show picric acid degrading activity in vitro, there is little evidence that these organisms will function under in situ conditions. Additionally, no organism or group of organisms has been isolated that demonstrate complete degradation of picric acid. At present the art teaches that only partial degradation is possible and that some of the degradation products may also be harmful to the environment as mutagens. There remains a need, therefore, for an effective degradative process for picric acid and related compounds that will degrade those compounds completely and be effective in both the in vitro and in situ remediation of contaminated environments.

SUMMARY OF THE INVENTION

The present invention provides a consortium of microorganisms able to use nitrogen-containing phenol compounds as a sole carbon source and of completely degrading them so that no aromatic degradation products are detectable. Nitrogen-containing phenol compounds may include, but are not limited to ammonium picrate, picramic acid, 2,4-dinitrophenol (2,4-DNP), 2,5-dinitrophenol (2,5-DNP), 2,6-dinitrophenol (2,6-DNP), 3-aminophenol, 2-aminophenol, 4-aminophenol, 2,4,6-trinitrotoluene, mononitrophenols, and nitroaromatics.

The present invention further provides a method for degrading picric acid and related compounds by growing a consortium of microorganisms capable of the complete degradation of nitrogen-containing phenol compounds under suitable conditions.

BRIEF DESCRIPTION OF THE FIGURES AND BIOLOGICAL DEPOSITS

Figure 1:
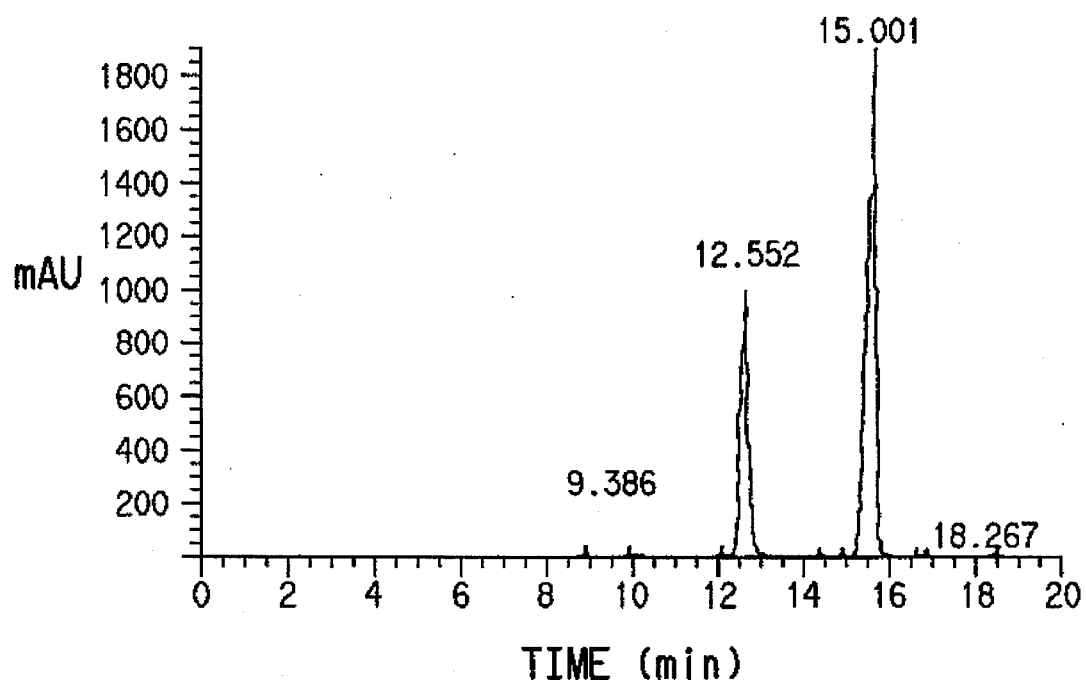
FIG. 1 is a typical HPLC elution profile showing retention times for picric acid, 2,4-dinitrophenol and nitrobenzene.

| Depositor Identification Reference | International Depository Designation | Date of Deposit |
| --- | --- | --- |
| Pic002 | ATCC 55381 | 18 December 1992 |
| Bm002 | ATCC 55382 | 18 December 1992 |

As used herein, "ATCC" refers to the American Type Culture Collection international depository located at 12301 Parklawn Drive, Rockville Md. 20852 U.S.A.

DETAILED DESCRIPTION OF THE INVENTION

As used herein the following terms may be used for interpretation of the claims and specification.

The term "contaminated environments" will refer to any environment contaminated with picric acid or related compounds. Typical contaminated environments may include, but are not limited to, soil, ground water, air, waste disposal sites, and waste streams.

The term "picric acid" will refer to the compound 2,4,6-trinitrophenol.

The term "nitrogen-containing phenol compounds" will refer to any phenol ring compound substituted with at least one $NO_2$ or $NH_2$ group or salts of the substituted compound. The phenol ring may also contain any other non-nitrogen chemical substitutions. Typical related compounds may include but are not limited to, ammonium picrate, picramic acid, 2,4-dinitrophenol (2,4-DNP), 2,5-dinitrophenol (2,5-DNP), 2,6-dinitrophenol (2,6-DNP), 3-aminophenol, 2-aminophenol, 4-aminophenol, 2,4,6-trinitrotoluene, mononitrophenols, and nitroaromatics.

The term "complete degradation" refers to the degradation of picric acid and related compounds to a point where no aromatic degradation products may be detectable.

The terms "microbial consortium" or "consortium" refers to any collection of microorganisms having at least two different species, capable of completely degrading picric acid and related compounds only when they occur together. The consortium may consist of many species of the same genera, many different genera of the same family or even members of different families of microorganisms.

The present invention relates to a novel consortium of microorganisms capable of the complete degradation of picric acid and related compounds and the use of said consortium for the remediation of picric acid from contaminated environments.

The microbial consortium of the present invention may consist of any combination of microorganisms where at least two different species are present. Most preferred is a consortium that includes, but is not limited to the bacterial species *Arthrobacter uratoxydans, Aurobacterium saperdae, Bacilllus cereus, Flavobacterium esteroaromaticum, Micrococcus luteus, Microccus varians, Methylobacterium mesophilicum, Pseudomonas putida,* and *Ochrobacterium anthropi.*

The consortium of the present invention was isolated from a waste treatment facility of an industrial site and selected by two methods. In the first method, a sample of waste material was inoculated into minimal medium supplemented with picric acid. The culture was subcultured into fresh medium three times at 100 h of culture. Each subculture was tested for its ability to degrade picric acid and related compounds.

In the second method, a sample of waste stream material was inoculated into minimal medium containing aniline waste stream effluent which contained about 2500 ppm picric acid. The final concentration of picric acid in the culture was 125 ppm. The culture was subcultured three times at 100 h of culture. Each subculture was tested for its ability to degrade picric acid and related compounds.

Figure 2:
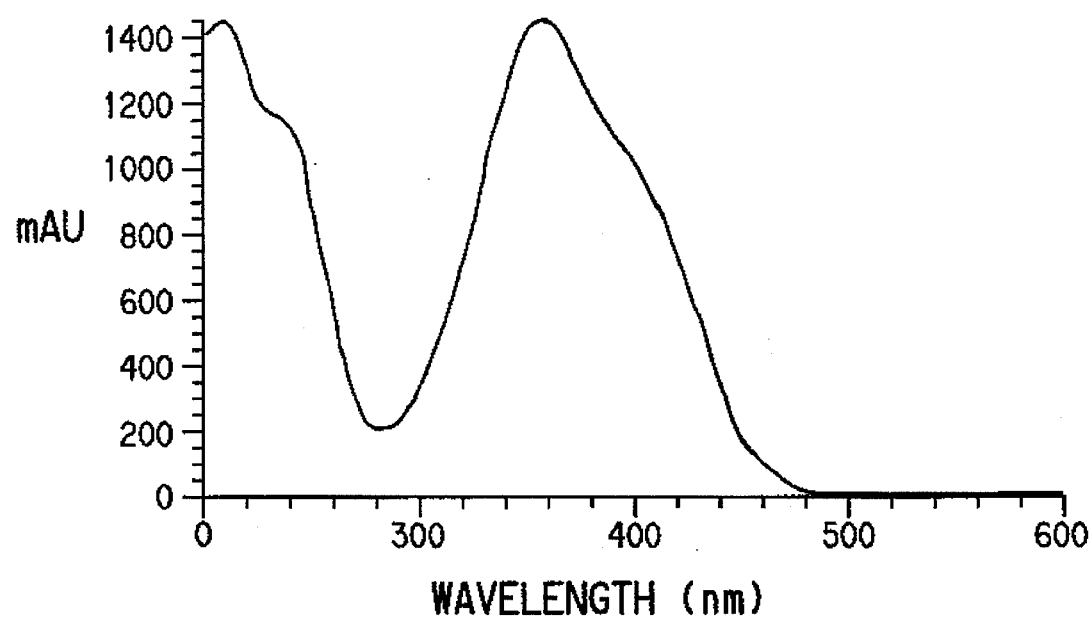
FIG. 2 is a typical scan of picric acid over a wavelength range of 200–600 nm.
Figure 3A:
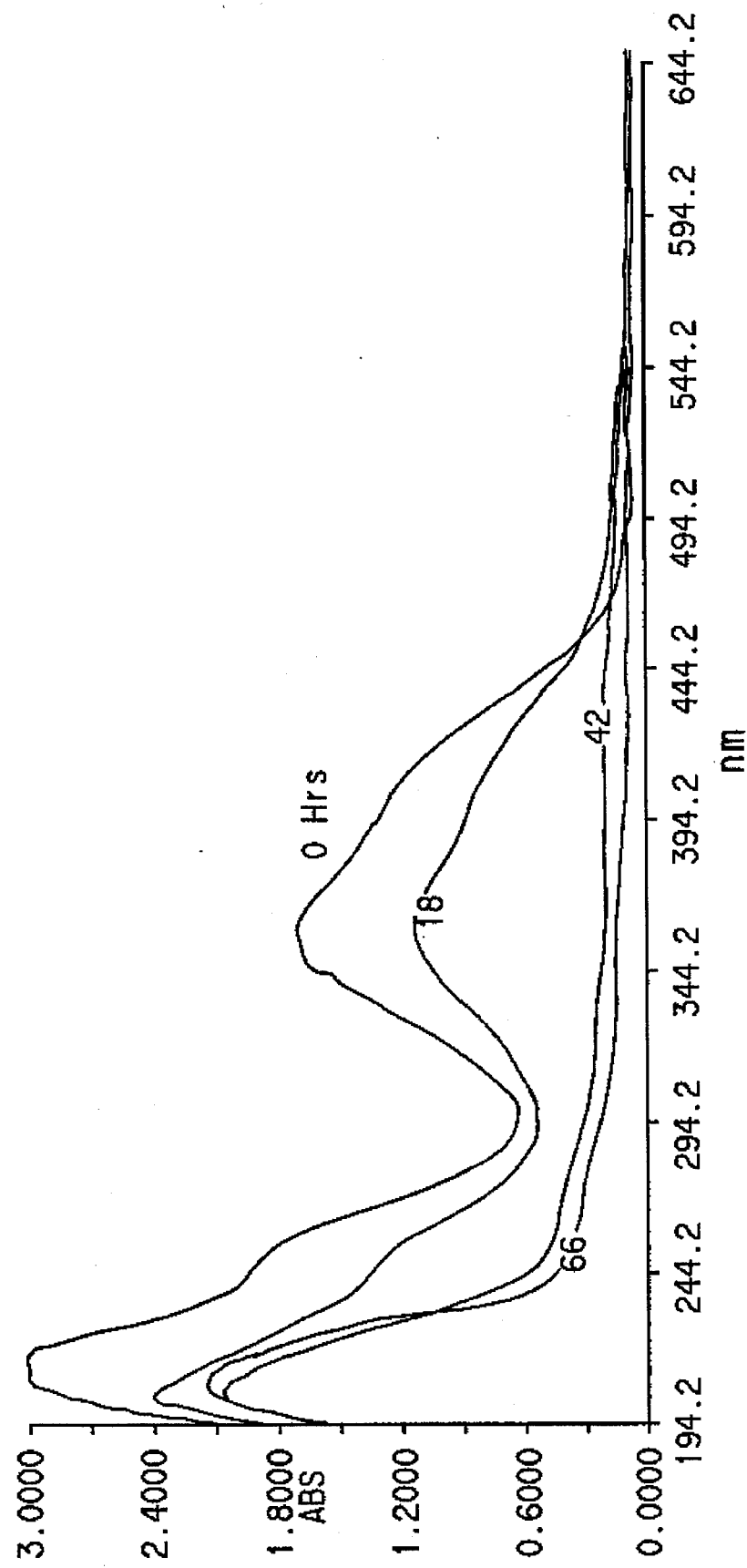
FIG. 3a is a scan over the wavelength range of 200–600 nm of media, diluted 1:4 with distilled water, from cultures containing picric acid.

The concentration of picric acid was monitored during culture over a 66 h period by HPLC using a diode-array detector. Scanning of picric acid over a wavelength range of 200–600 nm (FIG. 2) indicated a strong absorbance at 354.6 nm. Changes in absorbance at this wavelength were used to determine changes in concentration of picric acid. As can be seen in FIG. 3a, cultures containing inoculum from cells selected for growth in the presence of picric acid were able to completely degrade picric acid over a 66 h period. In similar fashion, data, illustrated in FIG. 3b, indicate that cultures containing cells grown in the presence of aniline waste stream effluent containing 2500 ppm picric acid (final concentration in culture, 125 ppm) also demonstrated the ability to completely degrade picric acid over a 66 h period.

Analysis of the isolates indicated that there were at least 9 different bacterial species present in the consortium including the species, *Arthrobacter uratoxydans, Aurobacterium saperdae, Bacilllus cereus, Flavobacterium esteroaromaticum, Micrococcus luteus, Microccus varians, Methylobacterium mesophilicum, Pseudomonas putida,* and *Ochrobacterium anthropi.*

No single member of the consortium demonstrated the ability to degrade picric acid when inoculated into medium containing either picric acid or aniline waste stream effluent as sole carbon source. It appears that it is necessary for a consortium of two or more of these microorganisms to remain together for complete picric acid degradation to occur.

The following examples are meant to illustrate the invention but should not be construed as limiting.

EXAMPLES

MATERIALS AND METHODS

Picric acid was obtained from Sigma as a 1% solution in water. HPLC separations were performed using an Hewlett Packard high performance liquid chromatograph (HPLC) model 1090 (Hewlett Packard, Valley Forge, Pa.). HPLC mobile phases were obtained from the Millipore Corporation (Bedford, Mass.) and were used as recommended by the manufacturer for the separation of organic nitrogen compounds. Spectrophotometric determinations were performed using a Perkin Elmer lambda 5 spectrophotometer, (Perkin-Elmer Corp., Greenwich, Conn.).

Example 1

ISOLATION OF BACTERIAL CONSORTIUM AND SELECTION FOR GROWTH ON PICRIC ACID

Samples of sludge which contained microorganisms were recovered from aerators at an industrial waste treatment facility. A first culture was constructed by inoculating a 5 ml sample into 25 ml of minimal medium (Table I) and adding 1.25 ml picric acid (1% solution in water). The culture was maintained at 30° C. with shaking for 100 h. The culture, 5 ml, was withdrawn and subcultured in 25 ml minimal medium supplemented with 1.25 ml picric acid as described above. Three successive subcultures were grown at 30° C. with shaking for 100 h. Cells collected from the third subculture were designated PIC002.

A second culture was constructed by inoculated a 5 ml sample into 25 ml of minimal medium and adding 1.5 ml of aniline waste stream effluent. The aniline waste stream effluent contained 2500 parts per million (ppm) of picric acid. The addition of aniline waste stream effluent to the culture medium resulted in a picric acid concentration of 125 ppm. The culture was maintained at 30° C. with shaking for 100 h. Five ml of culture were withdrawn and subcultured in 25 ml of minimal medium supplemented with 1.5 ml of aniline waste stream effluent. Three successive subcultures were grown at 30° C. with shaking for 100 h. Cells collected from the third subculture were designated Bm002. Pic002 and Bm002 were both found to contain a variety of different microorganisms.

Consortium designations Pic002 and Bm002 have been deposited with the American Type Culture Collection under the terms of the Budapest Treaty. Bacterial consortium Pic002 is assigned ATCC 55381. Bacterial consortium Bm002 is assigned ATCC 55382.

TABLE I

| Minimal medium (1) | | | Trace Elements (3) | |
|---|---|---|---|---|
| Compound | Wt in grams | Yeast extract (2) (10% Soln.) | Compound | Wt in grams |
| $K_2HPO_4$ | 6 | | $MgSO_4.7H_2O$ | 2 |
| $KH_2PO_4$ | 4 | | $CaCl_2$ | 0.4 |
| $NH_4Cl$ | 3.2 | | $MnSO_4$ | 0.08 |
| (Make to 1 liter with double distilled water, pH 7.2–7.3) | | | $FeSO_4.7H_2O$ | 0.05 |
| | | | $Na_2MoO_4.3H_2O$ | 0.15 |
| | | | (Make to 100 ml with double distilled water and add 1 ml conc. HCl) | |

To 1 L of (1) add 5 ml of (2) and 10 ml of (3). Add appropriate amounts of carbon source.

TABLE II

Approximate Aniline Waste Stream Effluent Composition

| Compound | Concentration |
|---|---|
| Ammonium picrate | 2500 ppm |
| Ammonium dinitrophenol | 300 ppm |
| Nitrobenzene | <50 ppm |
| Benzene | <10 ppm |
| Aniline | <50 ppm |

Example 2

DEGRADATION OF PICRIC ACID BY CONSORTIUM

HPLC analysis and detection: Identification of picric acid and related compounds was accomplished using Hewlett Packard HPLC, model 1090 (Hewlett Packard, Valley Forge, Pa.) with an attached diode-array detector. Separations of picric acid and break-down products were carried out on a ZORBAX SB-C8 column (E. I. du Pont de Nemours and Company, Wilmington, Del.) with column guard employing a gradient with two mobile phases. Mobile phase A consisted of PIC A low UV reagent 0.005M solution in double distilled water (Tetrabutyl Ammonium Phosphate) (Millipore Corp., Bedford, Mass.). The second mobile phase, B, was HPLC grade methanol. Mobile phases were combined for a standard separation run according the following protocol:

| Minutes | % A | % B |
|---|---|---|
| 1 | 55 | 45 |
| 7 | 55 | 45 |
| 20 | 20 | 80 |
| 10 | 55 | 45 |

Samples of cell free medium were analyzed by a diode-array detector using a sample wavelength of 254 nm and a reference wavelength of 450 nm. Using this protocol it was possible to separate and quantify picric acid, 2,4-dinitrophenol and nitrobenzene. A typical HPLC elution is shown in FIG. 1. As can be seen by the data in FIG. 1, 2,4-dinitrophenol elutes at a retention time of about 9.4 min., nitrobenzene elutes at a retention time of about 12.5 min. and picric acid elutes at a retention time of about 14 min.

Spectral analysis on cell free medium samples was done to confirm the change in picric acid concentration. It was determined that picric acid absorbed maximally at a wavelength of 354.6 nm. A typical spectral scan of picric acid over a wavelength range of 200–600 nm is shown in FIG. 2.

Figure 3B:
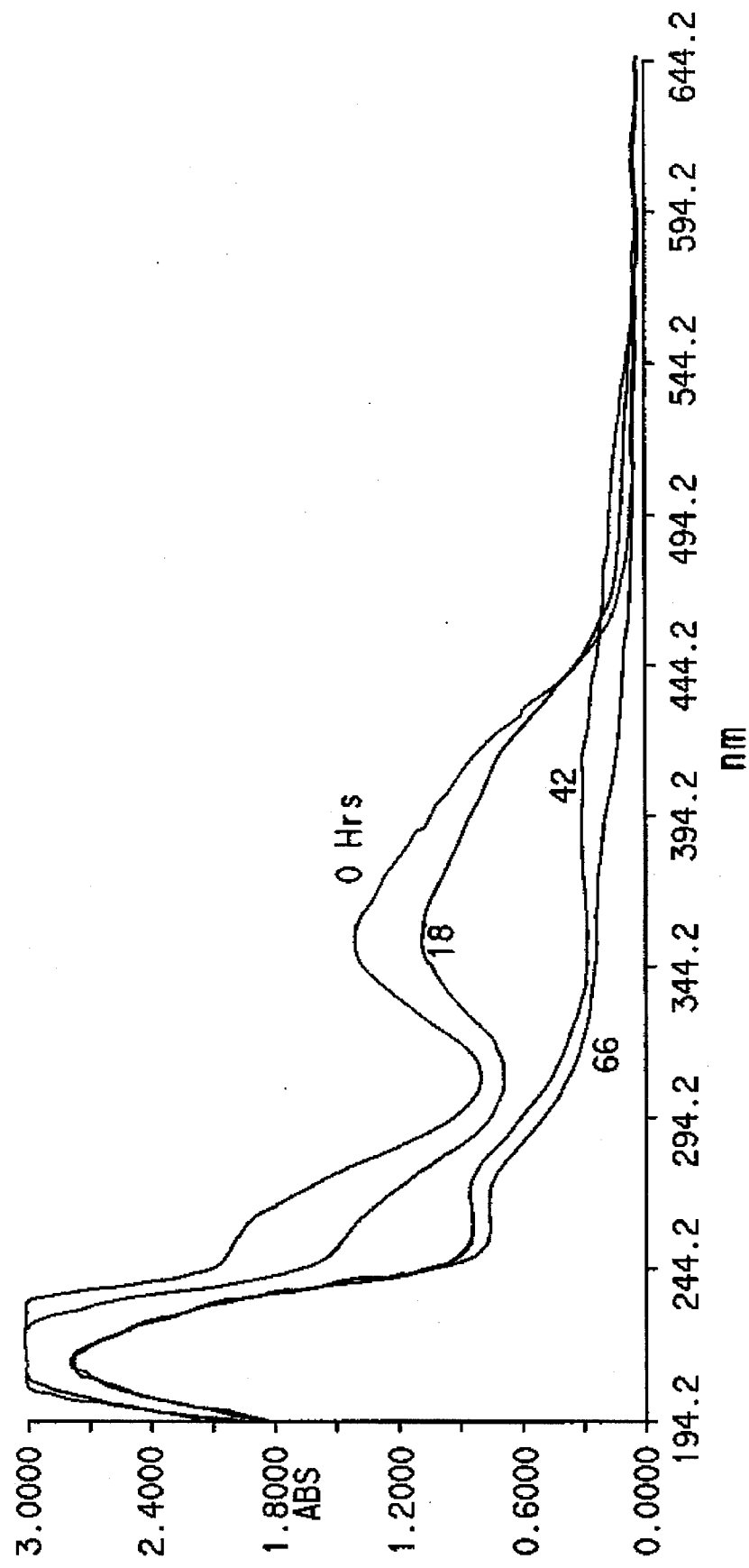
FIG. 3b is a scan over the wavelength range of 200–600 nm of media, diluted 1:4 with distilled water, from cultures containing aniline waste stream effluent.

Picric acid degradation:

Bacterial culture Pic002 was grown up in medium containing 125 ppm of picric acid. Bacterial culture Bm002 was grown in medium containing a 20 fold dilution of aniline waste stream effluent (final concentration of picric acid, 125 ppm) as a carbon source. Both sets of cultures were grown at 30° C. with shaking for 100 h. Five ml of each culture was inoculated into 25 ml of fresh medium and allowed to grow over a 66 h period at 30° C. Control media containing no inoculum of cell were incubated under identical conditions. Samples were removed at 0, 18, 42, and 66 h and analyzed by HPLC and by spectrophotometry over a range of ultraviolet and visual wavelengths for the presence of picric acid. Results are shown in FIGS. 3a and 3b. FIG. 3a shows a scan over 200–600 nm of samples taken from Pic002 cultures grown in the presence of picric acid and demonstrates a decline in the absorbance spectrum at 354.6 nm from 1.8 at 0 h to baseline at 66 h indicating complete degradation of picric acid in the cultures. FIG. 3b shows a similar scan of samples taken from Bm002 cultures grown in the presence of aniline waste stream effluent containing a final concentration of 125 ppm picric acid and also demonstrates complete degradation of picric acid in the sample by the inoculum.

To determine if degradation of picric acid was complete, samples of the 66 h cultures from both Pic002 and Bm002 cultures were analyzed on a Micromass mass spectrophotometer coupled to a Varian Vista 600 gas chromatograph equipped with 30 meter DB-1 (methylsilicon Megabore, 0.53 mm i.d.) column, programmed at a temperature gradient of 100°–275° C. (10° C./min.) for the following potential picric acid degradation products: nitrocatechol, picramic acid, 2,4-DNP, 2,5-DNP, 2,6-DNP, nitrobenzene, and aminophenol.

The analysis indicated that none of the above picric acid degradation products could be detected in the 66 h culture of either Pic002 or Bm002. This indicated the surprising result that the consortium of microorganisms is able not only to denitrify picric acid but also to perform ring opening reactions and degrade the compound completely using the breakdown products as alternate carbon sources.

Example 3

ANALYSIS OF BIOCHEMICAL ABILITY OF ISOLATES WITH RESPECT TO PICRIC ACID

Cultures of the bacterial consortia, Pic002 and Bm002 were streaked on R2A (Difco) medium and individual colonies were picked and re-plated on the same medium to confirm the individuality of the colonies. Each colony was subjected to analysis of fatty acid composition by gas chromatography for identification of individual species. Cultures were grown on a standard trypticase soy broth base in the presence of brain-heart infusions with supplements. Following culture in broth, the microorganisms were subjected to saponification in sodium hydroxide, followed by methylation in HCl and methanol, and finally fatty acid extraction into hexane and methyl tert-butyl ether. Gas chromatography of the extracted fatty acids reveals profiles of 9–20 carbon fatty acids in patterns typical of various genera and species of bacteria. Nine different bacterial species were identified in the consortium corresponding to individual colonies and were identified as, *Arthrobacter uratoxydans, Aurobacterium saperdae, Bacilllus cereus, Flavobacterium esteroaromaticum, Micrococcus luteus, Microccus varians, Methylobacterium mesophilicum, Pseudomonas putida*, and *Ochrobacterium anthropi*. Each species was tested for its ability to degrade picric acid in isolated form, away from the other members of the consortium.

One colony from each species, isolated as above, was inoculated into 10 ml of the medium described in Table I, supplemented with picric acid to a final concentration of 125 ppm. Cultures were incubated for 72 h at 30° C. and inspected visually for metabolism of picric acid. At a final concentration of 125 ppm in medium, picric acid gives a strong yellow color. The first indication of the metabolism of picric acid by bacterial cultures is a decrease in the intensity and quality of the yellow color. After a 72 h incubation none of the cultures of isolates demonstrated any color variation, indicating that picric acid was not being metabolized. Samples of the medium were subjected to HPLC and UV photospectrometric analysis as described in Example 2 and it was determined that no degradation of picric acid had taken place. These data suggest that at least some of the members of the consortia need to be cultured together for the degradation of picric acid to occur and that none of the individual members of the consortium are able to degrade picric acid, in isolation from the other members of the consortium.

What is claimed is:

1. A consortium of microorganisms identified as ATCC 55381 and comprising the bacterial genera Arthrobacter, Aurobacterium, and Pseudomonas, said consortium being isolated from waste treatment sludge and being capable of completely degrading picric acid.

2. A consortium of microorganisms identified as ATCC 55382 and comprising the bacterial genera Arthrobacter, Aurobacterium, and Pseudomonas, said consortium being isolated from waste treatment sludge and being capable of completely degrading picric acid.

* * * * *